(12) United States Patent
Hsia et al.

(10) Patent No.: US 11,951,091 B2
(45) Date of Patent: Apr. 9, 2024

(54) COMPLEX, CONTRAST AGENT AND METHOD FOR TREATING A DISEASE RELATED TO CXCR4 RECEPTOR

(71) Applicant: Institute of Nuclear Energy Research, Atomic Energy Council, Executive Yuan, R.O.C, Taoyuan (TW)

(72) Inventors: Chien-Chung Hsia, Taoyuan (TW); Chung-Hsin Yeh, Taoyuan (TW); Cheng-Liang Peng, Taoyuan (TW); Chun-Tang Chen, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 610 days.

(21) Appl. No.: 17/126,364

(22) Filed: Dec. 18, 2020

(65) Prior Publication Data

US 2022/0125761 A1    Apr. 28, 2022

(30) Foreign Application Priority Data

Oct. 27, 2020   (TW) .................................. 109137179

(51) Int. Cl.
*A61K 31/395*    (2006.01)
*C01G 15/00*    (2006.01)

(52) U.S. Cl.
CPC ............ *A61K 31/395* (2013.01); *C01G 15/00* (2013.01)

(58) Field of Classification Search
CPC ........................... A61K 51/0455; C01G 15/00
See application file for complete search history.

(56) References Cited

PUBLICATIONS

The influence of different metal-chelate conjugates of pentixafor on the CXCR4 affinity Poschenrieder et al. EJNMMI Research (2016) 6:36 (Year: 2016).*
Azamacrocyclic Metal Complexes as CXCR4 Antagonists Tanaka et al. ChemMedChem 2011, 6, 834-839 (Year: 2011).*

* cited by examiner

*Primary Examiner* — Jeffrey S Lundgren
*Assistant Examiner* — Eric Tran
(74) *Attorney, Agent, or Firm* — Locke Lord LLP; Tim Tingkang Xia, Esq.

(57) ABSTRACT

Disclosed herein is a complex, a contrast agent and the method for treating a disease related to CXCR4 receptor. The complex is configured to bind the CXCR4 receptor, and is used as a medicament for diagnosis and treatment of cancers and other indications related to the CXCR4 receptor.

7 Claims, 4 Drawing Sheets

COMPLEX, CONTRAST AGENT AND METHOD FOR TREATING A DISEASE RELATED TO CXCR4 RECEPTOR

CROSS REFERENCE TO RELATED APPLICATION

This application claims the benefits of Taiwan application Serial No. 109137179, filed on Oct. 27, 2020, the disclosures of which are incorporated by references herein in its entirety.

TECHNICAL FIELD

The present invention relates to the field of medical imaging, and in particular, to a complex capable of binding C-X-C chemokine receptor type 4 (CXCR-4, also known as fusin or CD184).

BACKGROUND

Malignant tumors are a major public health issue encountered by contemporary humans. With the increasing incidence of cancers all over the world, they have become a major subject that needs to be faced with by governments around the world. In recent years, with the improvement of medical technologies and the advancement of medical research, the rapid increase in the number of cancer patients can be slowed down, and a cure rate and a survival rate can be improved by early diagnosis and proper treatment. In addition, cardiovascular diseases caused by atherosclerosis have become the number one in top ten leading causes of death worldwide. Early diagnosis and early treatment will be critical issues in decreasing mortality.

CXCR4 chemokine receptor plays an important role in the mechanism of the body, and is associated with growth and development, angiogenesis, tumorigenesis and metastasis. Researches indicate that CXCR4 is expressed in multiple types of cells. By taking acute myelogenous leukemia (AML) as an example, the cells expressing CXCR4 are chemotactic, and attach to bone marrow stromal cells, resulting in poor chemotherapeutic outcome. Furthermore, other cancers also have similar research results, for example, lung cancer, skin cancer, breast cancer, urothelial carcinoma and glioma. In addition, other diseases are also strongly related to CXCR4. For example, atherosclerosis is a vascular inflammation caused by hyperlipidemia in the body, causing aggregation of a large number of immune cells capable of expressing CXCR4. Therefore, CXCR4 plays an important role in a pathogenic process.

In view of this, there is an urgent need in the art for a medicament capable of diagnosing or treating the disease related to overexpression of CXCR4, so as to improve defects of the related art.

SUMMARY

In order to make readers understand the basic meaning of the disclosure, the section of Summary provides a brief description of the disclosure. The section of Summary is not a complete description of the disclosure, and it is not intended to define the technical features or the scope of claims of the present invention.

An aspect of the present disclosure relates to a complex, configured to bind a CXCR4 receptor, comprising the following structure:

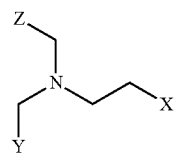

where X is a chelating group, such as a metal ion chelating agent, selected from a group consisting of: 1,4,7-triazacyclononane-N,N',N''-triacetic acid (NOTA), 1,4,7,10-tetraazacyclododecane-1,4,7,10-tetraacetic acid (DOTA), diethylenetriaminepentaacetic acid (DTPA), 1,4,8,11-tetraazacyclotetradecane-N,N',N'',N'''-tetraacetic acid (TETA), 1,4,7-triazacyclononane phosphinic acid (TRAP) and ethylenediaminetetraacetic acid (EDTA);

Y is

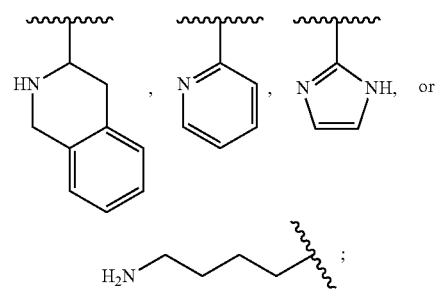

and

Z is

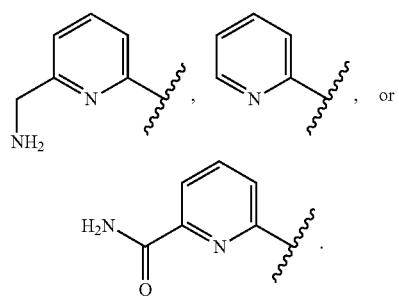

In an optional implementation, the complex is an example of the foregoing combination, and has a structure as follows:

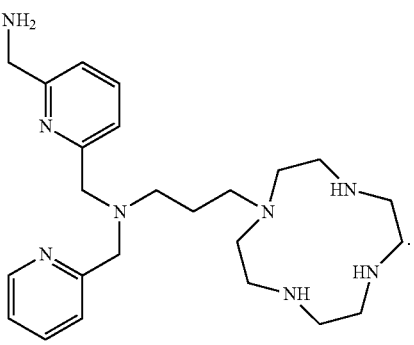

According to an implementation of the present invention, the complex further comprises a radioactive metal nuclide or a non-radioactive metal nuclide labeled on the complex of formula (I). In a specific implementation, the radioactive metal nuclide is indium-111, lutetium-177, gallium-68, gallium-67, yttrium-90 or copper-64, or the like, and a non-radioactive metal ion is gadolinium or the like. According to a specific implementation, the radioactive metal nuclide is indium-111.

Another aspect of the present invention relates to a contrast agent, comprising the complex shown in any of the foregoing implementations; and a contrast excipient.

Still another aspect of the present invention relates to a method of using the complex shown in any of the foregoing implementations to diagnose or treat a disease related to CXCR4.

In an optional implementation, the disease is a cancer, and is selected from a group consisting of: lymphoma, multiple myeloma, testicular cancer, thyroid cancer, prostate cancer, throat cancer, cervical cancer, nasopharynx cancer, breast cancer, colorectal cancer, pancreatic cancer, gastric cancer, head-and-neck cancer, esophageal cancer, rectal cancer, bladder cancer, kidney cancer, lung cancer, liver cancer, brain cancer, melanoma and skin cancer.

In other implementations, the disease is an immune disease, an infectious disease, a cardiovascular disease or an inflammatory disease.

Those of ordinary skill in the art the invention belongs to can fully learn the central concept, the techniques used and various implementations of the invention with reference to the detailed description as follows.

BRIEF DESCRIPTION OF THE DRAWINGS

To make the foregoing and other objects, features, advantages, and examples of the present invention more comprehensibly, the drawings are described as follows.

DETAILED DESCRIPTION OF DISCLOSED EMBODIMENTS

Figure 1:
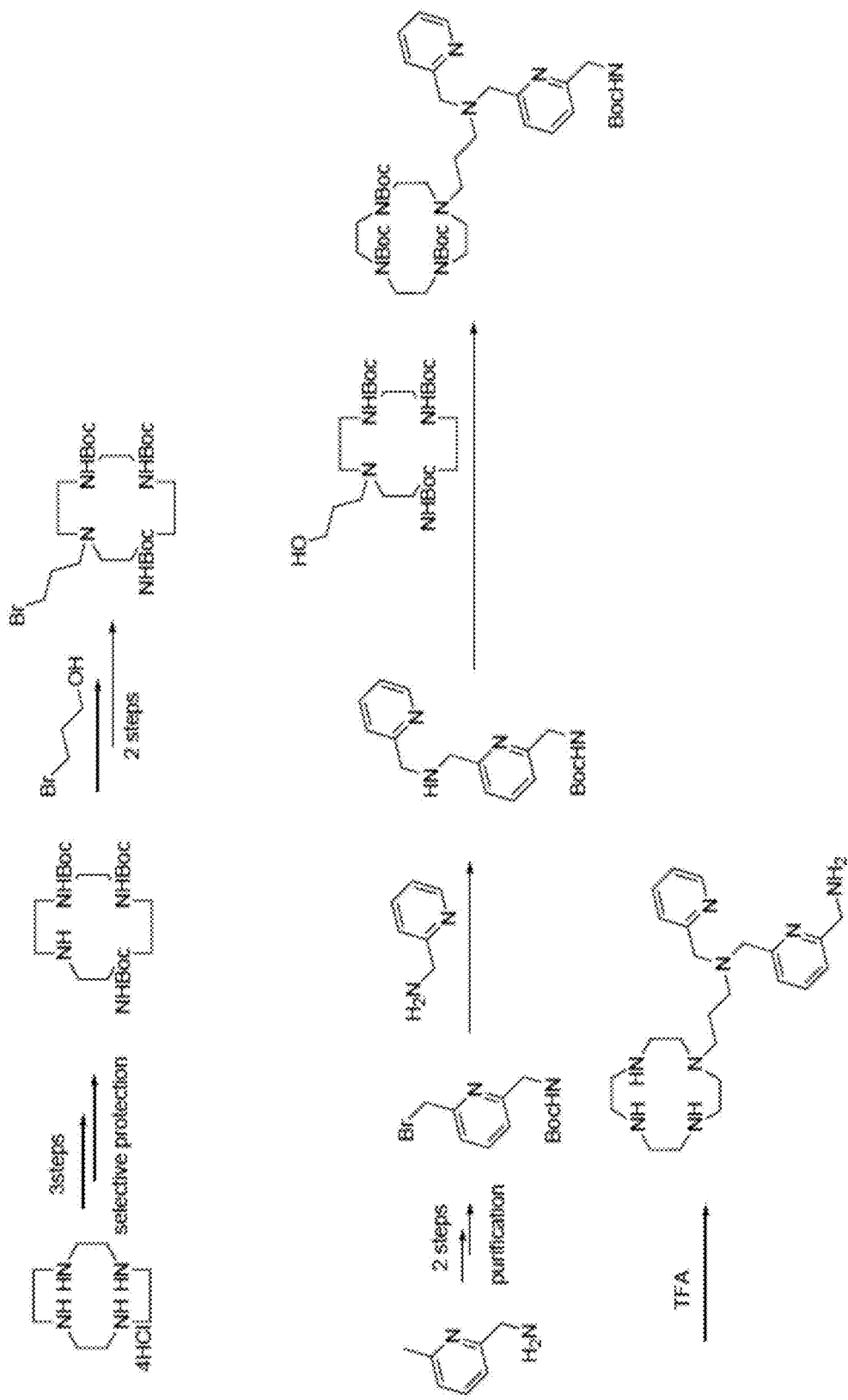
FIG. 1 is a flowchart of synthesizing a complex of the present disclosure according to an implementation of the present invention.

To make the description of the present disclosure more detailed and complete, the following provides an illustrative text description of the implementations and specific examples of the present invention; but the implementations and specific examples of the present invention are not limited thereto.

Unless otherwise stated, the scientific and technical terms used in this specification have the same meanings as those understood and commonly used by a person of ordinary skill in the art. In addition, nouns used in this specification include the singular and plural forms of the nouns, unless otherwise specified.

The word "individual" or "patient" refers to an animal capable of receiving a complex of the present invention. In a preferable implementation, the animal is a mammal, and in particular, is a human.

The word "disease" herein is a disease related to CXCR4. Specifically, cells expressing CXCR4 participate in the pathogenesis of the disease, causing the development of the disease or symptoms related to the disease. For example, the "disease" may include tumors expressing CXCR4, or is caused by lymphocytes, monocytes and macrophages expressing CXCR4.

The "cancer" may be a non-solid tumor or a solid tumor. For example, the cancer includes, but is not limited to tumors expressing CXCR4, such as lymphoma, multiple myeloma, testicular cancer, thyroid cancer, prostate cancer, throat cancer, cervical cancer, nasopharynx cancer, breast cancer, colorectal cancer, pancreatic cancer, gastric cancer, head-and-neck cancer, esophageal cancer, rectal cancer, bladder cancer, kidney cancer, lung cancer, liver cancer, brain cancer, melanoma and skin cancer.

As described in this specification, the term "about" generally means that an actual value falls within plus or minus 10%, 5%, 1%, or 0.5% of a specific value or range. The term "about" herein means that an actual value falls within an acceptable standard error of an average value, depending on the consideration of a person of ordinary skill in the art the present invention pertains. Except for experiment examples, or unless otherwise clearly stated, it should be understood that the ranges, quantities, numerical values, and percentages used herein are all modified by "about". Therefore, unless otherwise stated, the values or parameters disclosed in this specification and the appended claims are all approximate values, and may be changed as required.

To resolve the problems existing in the related art, the present inventor provides a novel complex configured to bind CXCR4 for the first time, and the complex mainly has a structure as shown in the complex of formula (I):

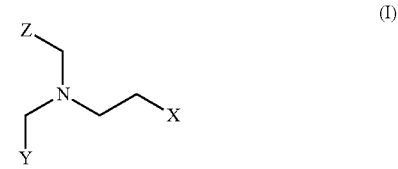

where X is a chelating group, such as a metal ion chelating agent, selected from a group consisting of: 1,4,7-triazacyclononane-N,N',N''-triacetic acid (NOTA), 1,4,7,10-tetraazacyclododecane-1,4,7,10-tetraacetic acid (DOTA), diethylenetriaminepentaacetic acid (DTPA), 1,4,8,11-tetraazacyclotetradecane-N,N',N'',N'''-tetraacetic acid (TETA), 1,4,7-triazacyclononane phosphinic acid (TRAP) and ethylenediaminetetraacetic acid (EDTA);

Y is

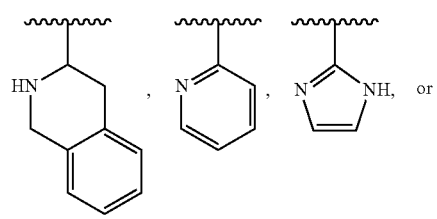

-continued

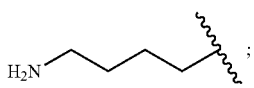

and
Z is

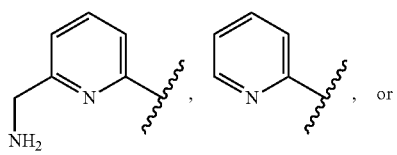

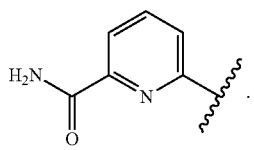

The structure of the complex of the present invention may bind to the positions of specific amino acids of CXCR4, as determined by bioinformatics analysis. Compared with conventional small molecular drugs (e.g., AMD3100), the complex provided in the present invention has a stronger ability of binding a CXCR4 receptor. Through calculation and analysis, binding energy of the complex is much lower than that of AMD3100, so that the specificity of a drug can be improved. In addition, the complex of the present invention adds a metal ion chelating agent in the structure, so that it can be labeled with radioactive metal ions or non-radioactive metal ions, and may be used for SPECT/PET medical imaging or used as an MRI contrast agent.

Furthermore, in an example of the present invention, the experiment results in a tumor animal model show that compared with commercially available CXCR4 antagonists (e.g., AMD3100), the complex of the present invention has a significantly higher aggregation amount in tumors. Therefore, it can be confirmed that the complex of the present invention has potential to be a medicament for diagnosing or treating a disease related to CXCR4.

According to an implementation of the present invention, the complex provided in the present invention can effectively bind to cells expressing CXCR4. Therefore, regardless of cancers or other diseases related to CXCR4 (for example, cardiovascular disease, inflammatory disease or immune disease), the diseases can be effectively diagnosed or treated by using the complex.

A plurality of examples is disclosed below to illustrate various different implementations of the present invention, so that those with ordinary knowledge in the technical field of the present invention can implement the technical content disclosed in the present invention according to the disclosure of the specification. Therefore, the examples disclosed below should not be used to limit the scope of the claims of the present invention.

Example 1. Synthesis of a Complex APD of the Present Invention

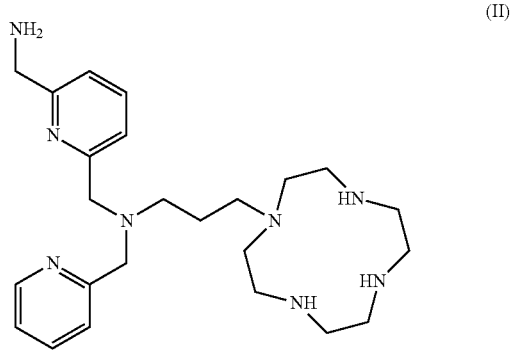 [SMILES: NCc1cccc(CN(CCCN2CCNCCNCCNCC2)Cc2ccccn2)n1]

(II)

Figure 2:
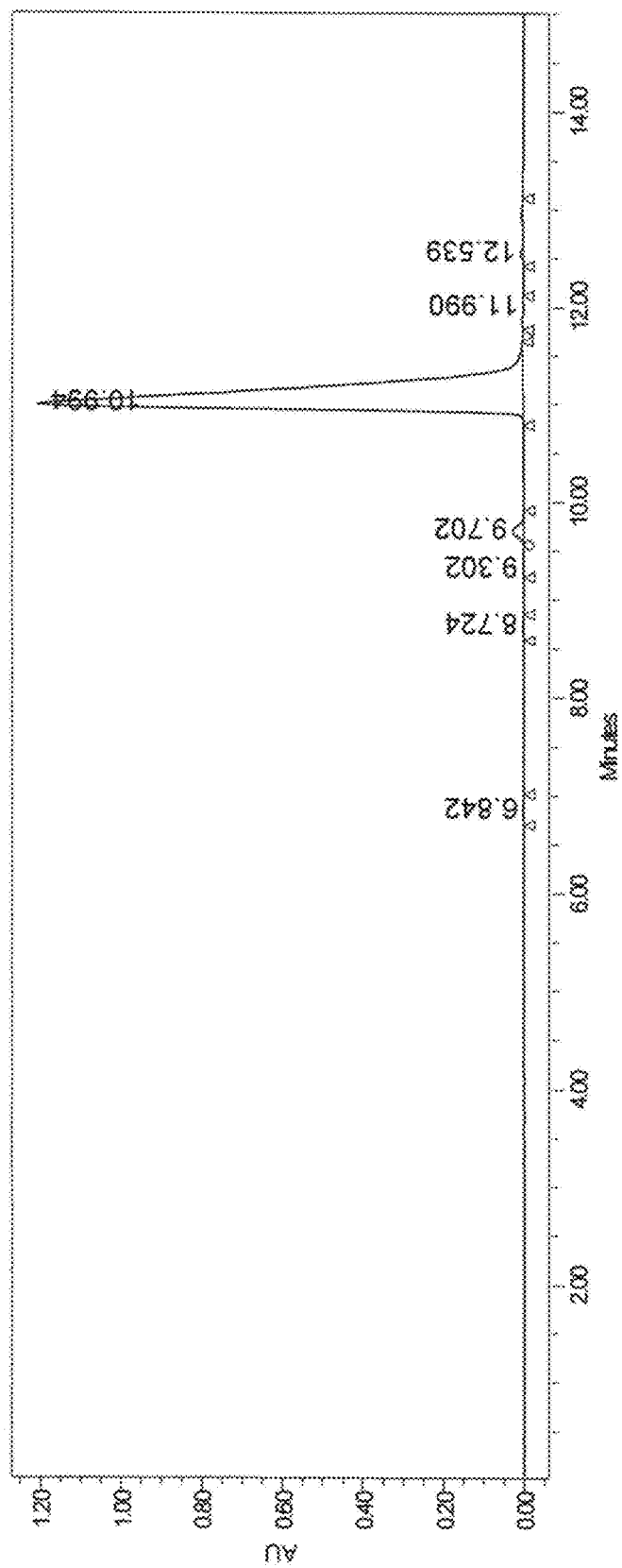
FIG. 2 is an HPLC chromatogram of a complex of the present disclosure according to an implementation of the present invention.
Figure 3:
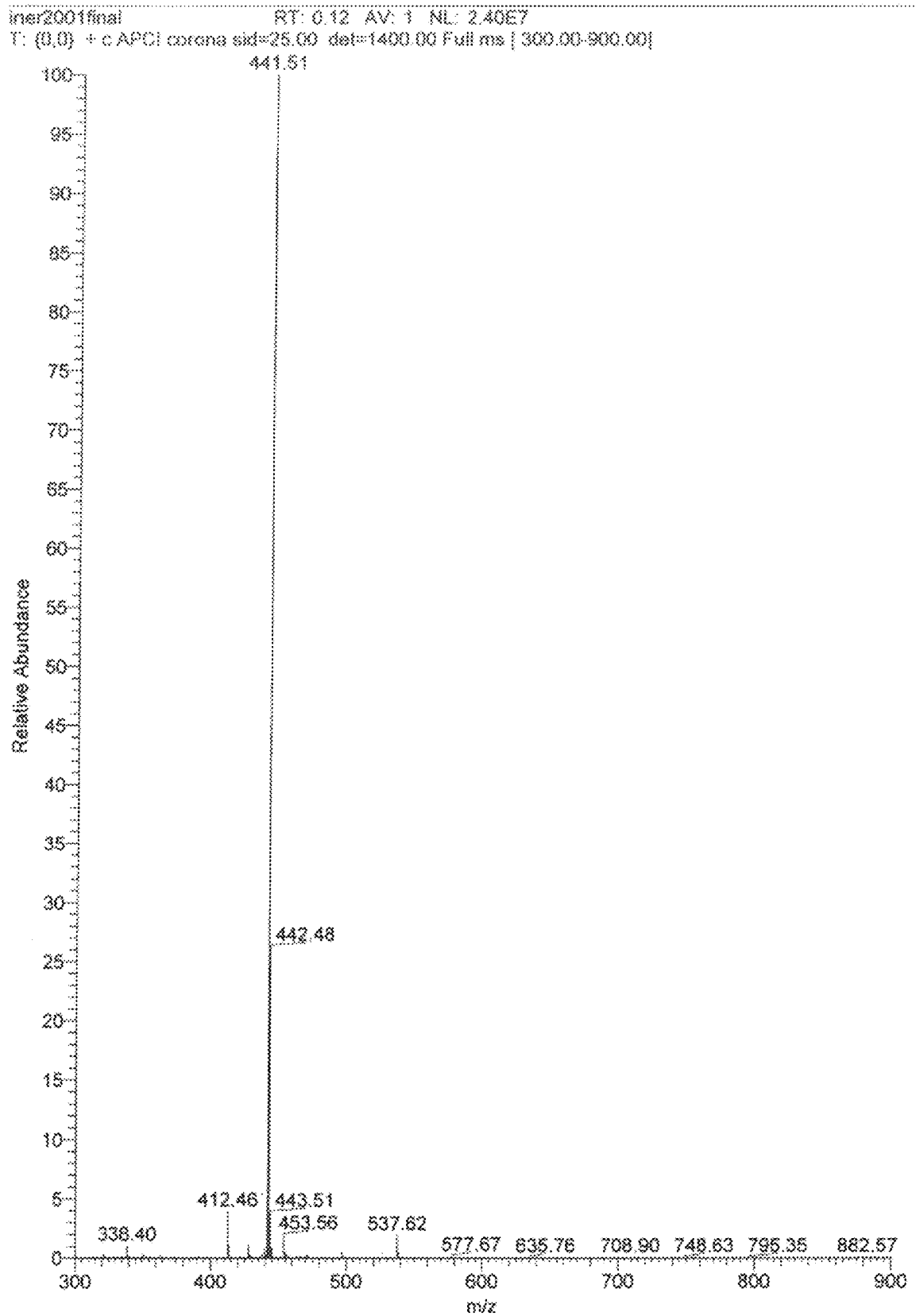
FIG. 3 is a mass spectrum of a complex of the present disclosure according to an implementation of the present invention.

A complex of Formula (II) of the invention is submitted to Jinsheng company for synthesis, and synthesizing steps are referred to FIG. 1. Analysis results of synthetic products by HPLC and mass spectrometry (MS) are shown in FIG. 2 to FIG. 3, where the analysis data of NMR is Aromatic H: 7.2~8.4, N—$CH_2CH_2$—N H: 2.2~2.7, C—$CH_2$—C H: 1.6, N—$CH_2$—C H: 3.7~3.8, N—$CH_2$-ar. H: 4.8. HPLC results show that the peak time of the main component is 11.0 min; the content percentage (chromatographic purity) is 97.52% (>95%). The mass spectrum of the parent molecular ion of the main component is: $[M+H]^+$ m/z=441, in line with the main component.

Example 2. A Complex APD of the Present Invention Labeled with In-111

5 μg to 50 μg of the complex APD of Example 1 is reacted with 1 mCi to 10 mCi of In-111 (with a specific activity greater than 50 mCi/mL) in citrate/acetate buffer solution (pH 3.5~6.5) at 50° C. to 95° C. for 10 min to 30 min, to obtain a product, the complex APD labeled with In-111.

Instant thin layer chromatography (iTLC) is used to analyze the efficiency of radioactive labeling, and results show that the labeling efficiency is greater than 95%.

Example 3. Analysis of Binding Efficacy of the Complex APD of the Present Invention This experimental example uses BIOVIA software for analysis of binding energy, and results are calculated by docking the complex of the present invention and a control medicament TIQ-15 with amino acids at specific positions of CXCR4 (TRP94, HIS113, TYR116, ASP97, ALA98 and ILE185). See Table 1.

TABLE 1

|  | Binding energy |
| --- | --- |
| TIQ-15 (an AMD3100 derivative) | −88 kcal/mol |
| APD | −300 kcal/mol |

The results show that the binding energy of the complex APD of the present invention is much lower than that of the control medicament, and thus it can be confirmed that the complex of the present invention has better sensitivity and specificity, and is suitable to be used as a medicament for diagnosing or treating cancers and other indications related to CXCR4.

Example 4. Evaluation of the Efficacy of the Radioactive Nuclide-Labeled Complex of the Present Invention by Using a Breast Cancer Animal Model 0.1 mCi to 0.5 mCi of the complex of the present invention is injected into mice with breast cancer tumors through tail vein. After biological distribution for 1 h to 6 h, single photon emission computed tomography (SPECT) is used for imaging.

Figure 4:
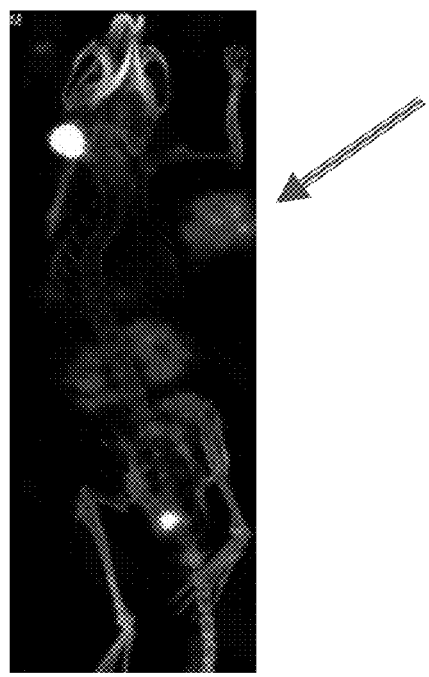
FIG. 4 is a NanoSPECT/CT image of a complex of the present disclosure in a breast cancer animal model according to an implementation of the present invention.

The result of this experimental example is shown in FIG. 4. The result shows that after two hours of the injection of the complex of the present invention, significant drug aggregation can be seen at the tumor site.

The specific examples disclosed above are not intended to limit the scope of the claims of the present invention. Those of ordinary skill in the art can make changes according to their common experience within the scope covered by the principles and spirit of the present invention. Therefore, the scope of rights claimed by the present invention should be subject to the scope defined by the claims.

What is claimed is:

1. A complex configured to bind CXCR4, comprising the following structures:

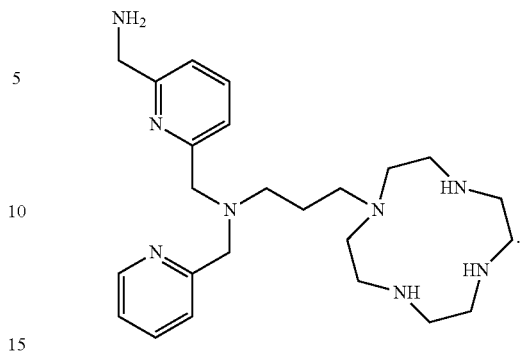

(II)

2. The complex according to claim 1, further comprising a radioactive metal nuclide or a non-radioactive metal labeled on the complex of formula QL.

3. The complex according to claim 2, wherein the radioactive metal nuclide is indium-111, lutetium-177, gallium-68, gallium-67, yttrium-90 or copper-64.

4. The complex according to claim 3, wherein the radioactive metal is indium-111.

5. A method of using the complex according to claim 1 treat or diagnose a disease related to CXCR4.

6. The method according to claim 5, wherein the disease is a cancer, and is selected from a group consisting of: lymphoma, multiple myeloma, testicular cancer, thyroid cancer, prostate cancer, throat cancer, cervical cancer, nasopharynx cancer, breast cancer, colorectal cancer, pancreatic cancer, gastric cancer, head-and-neck cancer, esophageal cancer, rectal cancer, bladder cancer, kidney cancer, lung cancer, liver cancer, brain cancer, melanoma and skin cancer.

7. The method according to claim 5, wherein the disease is an immune disease, an infectious disease, a cardiovascular disease or an inflammatory disease.

* * * * *